United States Patent [19]

Bryant

[11] Patent Number: 5,549,711
[45] Date of Patent: Aug. 27, 1996

[54] PROSTHETIC FOOT AND KEEL THEREFOR HAVING PROGRESSIVE STIFFENING UNDER INCREASING LOAD

[75] Inventor: William E. Bryant, Everett, Wash.

[73] Assignee: M+IND (Model + Instrument Development), Seattle, Wash.

[21] Appl. No.: 129,844

[22] Filed: Sep. 30, 1993

[51] Int. Cl.$^6$ .................................... A61F 2/66
[52] U.S. Cl. ............................ 623/53; 623/55
[58] Field of Search .................... 623/29, 47, 48, 623/49, 50, 52, 53, 55; 36/89

[56] References Cited

U.S. PATENT DOCUMENTS

| | | | |
|---|---|---|---|
| 518,658 | 4/1894 | Andrews | 623/50 |
| 3,754,286 | 8/1973 | Ryan | 623/26 |
| 4,328,594 | 5/1982 | Campbell et al. | 623/55 |
| 4,865,612 | 9/1989 | Arbogast et al. | 623/55 |
| 4,892,553 | 1/1990 | Prahl | 623/55 |
| 5,116,384 | 5/1992 | Wilson et al. | 623/49 |
| 5,152,082 | 10/1992 | Culpepper | 36/89 |

FOREIGN PATENT DOCUMENTS

| | | | |
|---|---|---|---|
| 90053080 | 12/1991 | Austria | 623/55 |
| 778732 | 12/1980 | U.S.S.R. | 623/55 |
| 1391643 | 4/1988 | U.S.S.R. | 623/53 |

*Primary Examiner*—David Isabella
*Assistant Examiner*—Laura Fossum
*Attorney, Agent, or Firm*—Seed and Berry

[57] ABSTRACT

A prosthetic foot having a keel formed by a flexible sole plate connected to the lower end of an ankle portion that is attachable to a user's leg or leg prosthesis. A plurality of resilient bending ribs extend from the angle portion to spaced apart locations on the upper surface of the sole plate to resiliently bias the sole plate to a neutral configuration. As the forward portion of the sole plate is progressively loaded, the sole plate flexes causing the bending ribs to deflect until they successively stack up against each other, thereby progressively stiffening the keel.

24 Claims, 7 Drawing Sheets

PROSTHETIC FOOT AND KEEL THEREFOR HAVING PROGRESSIVE STIFFENING UNDER INCREASING LOAD

TECHNICAL FIELD

The present invention relates to a prosthetic foot, and more particularly to a keel disposed within a foamed foot shaped elastomer cover and configured to provide an enhanced stability and comfort for light to moderate loads, such an associated with walking, and progressive stiffening under increasing loads to accommodate occasional high stress usage such as in running and jumping.

BACKGROUND OF THE INVENTION

A variety of prosthetic foot designs have been developed in recent, years to give more versatility to the user. Traditionally, prosthetic feet were constructed with relatively solid or rigid ankle blocks augmented by some for of elastic or flexible cushioning in the heal area such as often provided by a low density elastomeric foam under the solid ankle. This type of early prosthetic foot construction is known as the SACH foot as an acronym for "solid ankle cushion heel". The construction and functioning of the SACH foot offered comforting stability when the user is standing but did little to assist the user in walking, or moderate to athletic running and jumping. This early prosthetic foot standard had the feel of a "dead" foot lacking a natural quality of rebound or spring back and/or forward thrust to assist the gait of the wearer.

To improve upon the dynamic performance of the SACH foot, innovative foot designs offered various forms of energy storage in one or more various configurations of spring keels. Thus, more recent prosthetic feet with energy storage enabled natural interaction between the cyclic loading and unloading of the foot during body movement to more closely simulate the natural foot leg body gait. Examples of these recent dynamic response energy storage feet are found in U.S. Pat. Nos. 4,547,913 and 5,066,305. While the energy storage prosthetic foot has enjoyed great acceptance and increased the athletic range of users, there still remains a need for a less dynamic foot prosthesis; one that offers particular comfort in walking providing rollover ease and some energy storage and return to make the foot more lively than the traditional SACH's foot design.

In this regard, a dynamic response keel designed for the very active and athletic user exhibits a somewhat stiff feel and the user may have the uncomfortable sensation of vaulting over a stiff toe, i.e., difficulty in following through with forward rotation as the gait progresses to and through lift off. This is because the foot must rotate over the relatively stiff keel tip of the dynamic response keel compared to the older SACH foot.

Thus, it is an aspect of the present invention to provide an improvement over known prosthetic feet by providing greater stationary stability and more comfortable rollover feel especially during walking in a light to moderate energy storage and energy return foot so as to give a livelier sensation compared to the traditional SACH's foot. Another aspect in to provide an improved prosthetic foot with sharply progressive stiffening so as to not give way under occasional heavy load.

It is a further aspect of the present invention to provide an improved foot prosthesis having a structural design that accommodates a wide range of customizable stiffness, using the same basic keel configuration.

Still another aspect of the invention is to provide a keel design and prosthetic foot having the above improvements and configured in a geometry that is capable of being mass manufactured into a light weight product at a relatively low per unit cost by injection molding the keel as a unitary structure made up of thin walls.

SUMMARY OF THE INVENTION

In accordance with this invention, the prosthetic foot incorporates a keel structure having at least one bendable member having elastic properties that deforms under bending and axial compression. A plurality of such bendable members may also be used so that they stack up against each other to progressively stiffen the keel under increasing foot loads. The preferred embodiment has ankle, heel and forefoot portions. The ankle portion is adapted to receive an attachment means for joining the keel to a user's log or log prosthesis, and the forefoot portion has curved instep and bottom surfaces that commence at respective upper and lower extents of said ankle portion and it may curve forwardly and gently downwardly and converge toward and terminate at a tip of the keel lying near the ball of a foot. In this preferred embodiment, the bending members are integral with the keel forefoot and are formed by arcuate slots that define a plurality of normally spaced apart thin precurved walls (bending members) shaped and positioned so that with increasing body force on the foot and with resulting increasing keel deflection, the bending members react to bending and axial compression loads to deform in a manner that causes them to successively stack up against the next underlying member thereby progressively increasing the stiffness of the keel.

Also, in the preferred embodiment, the keel is injection molded from a synthetic polymer and the keel structure in accordance with this injection molding process is made up of relatively thin wall sections including the precurved bending members. The above configuration meets the injection molding process requirement of uniformly thin walls while maximizing deflection at the toe and accommodating a relatively high total load bearing capability at maximum design deflection due to the stacking function of the bending members.

For deflection, the multiple bending members undergo deformation under bending moments and axial compression. As load is applied to the keel near its tip, the members bend inwardly into small radii but still substantially smooth or continuous curves. Their precurved shape insures deformation of the bending members in an inward tightening (i.e. shortening radii) of the curvature. Individual stiffness of the bending members is kept relatively low on an individual member basis to allow a soft feel at the tip due to the greater bending moments exerted on the members by loads applied in the tip region prior to stacking of the members. As the members bend, they successively stack up causing the keel stiffness to increase progressively in the fully deflected condition at high stiffness, the keel members still assume smooth continuous curves eliminating points of high stress.

The geometry provides minimum stress in the keel by generating substantially constant bend radius over the length of the keel and spreading the load over multiple thin wall members. This allows the maximum amount of deflection at the toe without stress concentration within the keel. The bending members are loaded progressively, providing for low stiffness (i.e. softness) at walking loads with high stiffness at higher loads. The stiffness progressively increases with deflection.

As user's gait progresses from heel strike to push off, the load moves forward and the stiffness of the keel drops when the load moves onto the tip area in front of the forward most bending member. The keel deflects easily due to the initial low rigidity of the bending members until they begin to stack up against each other. This soft toe bending simulates flexion at the metatarsal-phalangeal joints.

Because of the stacking up of the bending members during increasing deflection, an alternative embodiment of the foot is made with selective stiffening material, such as an elastomeric foam injected into the slots between the bending members to selectively increase stiffness tailored to the patient's weight and level of activity.

In another alternative embodiment, one or more of the individual bending members are fabricated to be detachable and hence replaceable with like configured members of different material, thickness, or other properties to selectively tailor the foot to the user's needs.

A still different embodiment has a heal structure with another plurality of bending, stacking heal cushioning but progressive stiffening members for soft initial heel cushioning but progressive stiffening.

BRIEF DESCRIPTION OF THE DRAWINGS

The details of the embodiments of the present invention will be described in connection with the accompanying drawings, in which.

DETAILED DESCRIPTION OF THE INVENTION

Figure 1:
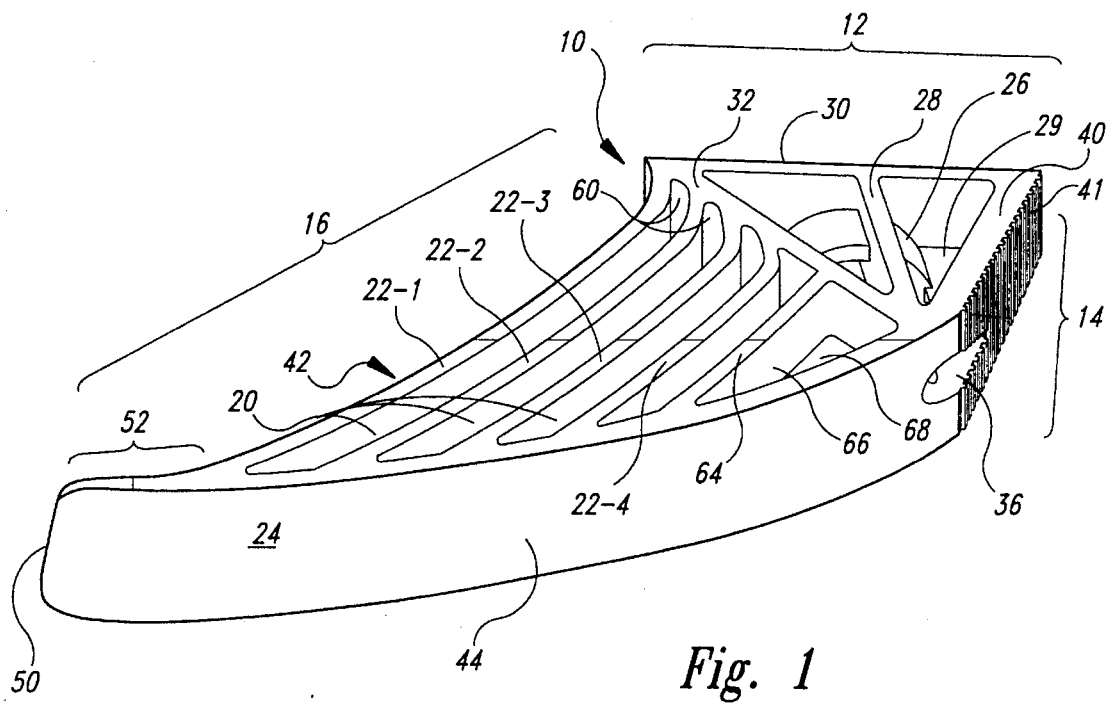
FIG. 1 is an isometric view of the preferred keel construction for use in a prosthetic foot in which the keel is to be covered by a relatively low density, elastic foam cosmesis in the general shape of a human foot.
Figure 2:
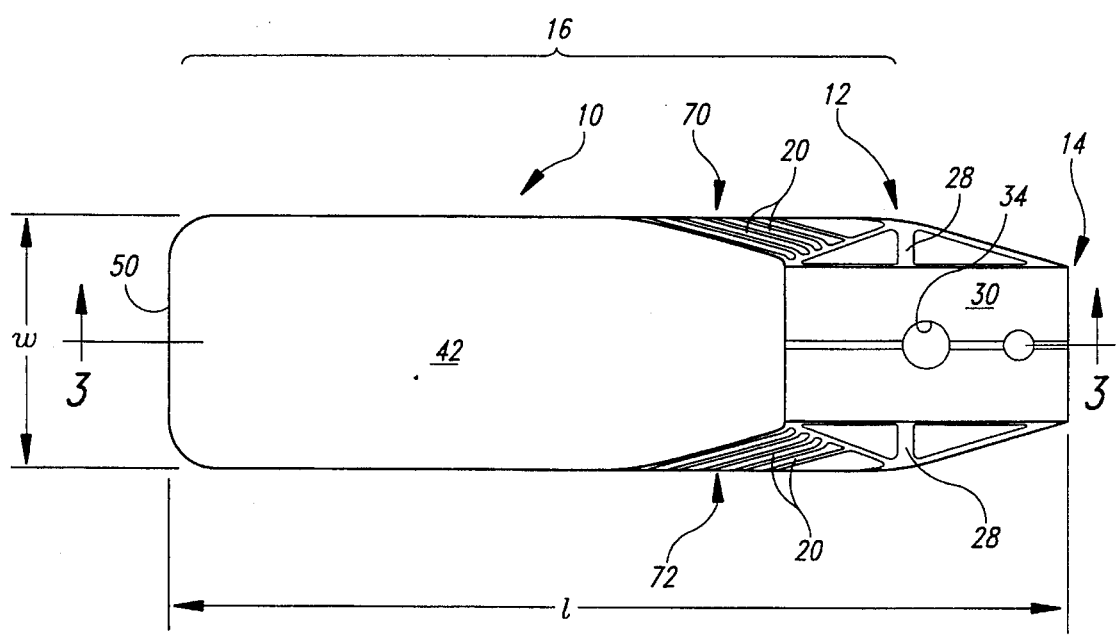
FIG. 2 is a top plan view of the keel of FIG. 1.
Figure 3:
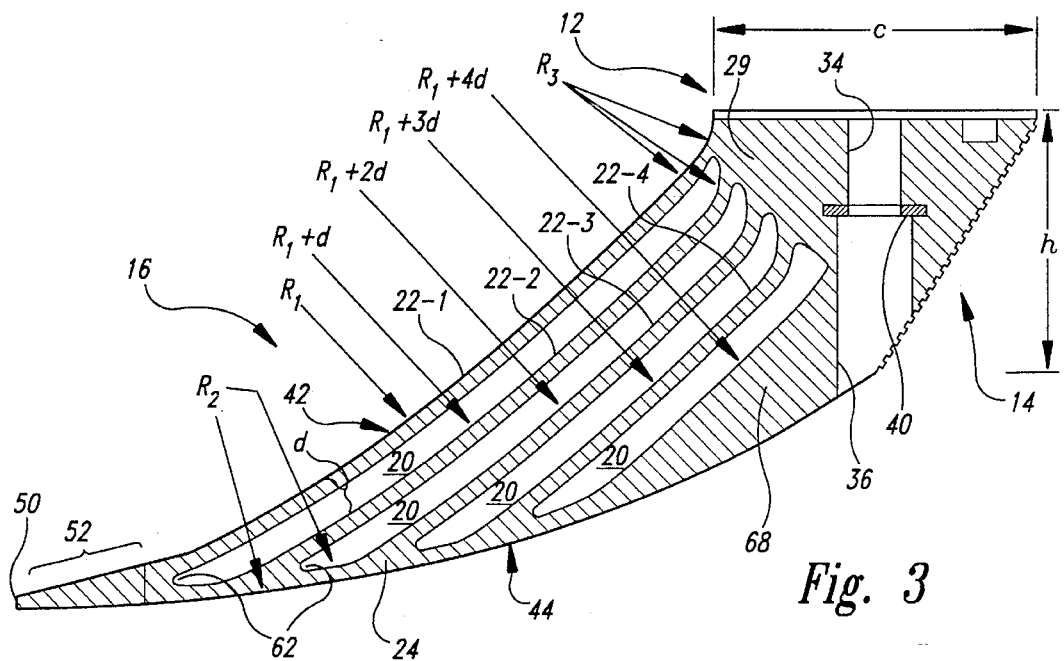
FIG. 3 is a vertical sectional view of the keel of FIG. 1 taken lengthwise of the keel at section line 2—2.

With reference to FIGS. 1 through 3, the prosthetic foot keel 10 in accordance with a preferred embodiment of the inventive keel is preferably formed as a unitary structure from a material having elastic properties. The keel 10 may be injection molded from a synthetic polymer.

More particularly, the presently preferred embodiment of the keel 10 a relatively rigid ankle portion indicated at 12, a diminished heel portion at 14, and a forefoot portion 16 that are made up of interconnected, thin walls such as characteristic of an injection molding process. This thin wall characteristic is uniquely utilized in the forefoot portion 16 of keel 10 by designing the mold (not shown) to form a plurality of arcuate slots 20 that in turn define a plurality of precurved thin bending walls or members 22a, 22b, 22c and 22d that join a precurved sole plate 24.

Ankle portion 12 is essentially made up of an annular injection molded wall structure 26, the interior of which defines a vertical bore for receiving a standard attachment bolt or pylon fastener (not shown) for connecting the keel to a user's leg or leg prosthesis. A suitable attachment fastener is, for example, shown in U.S. Pat. No. 5,066,305. Additionally, ankle portion 12 is given rigidity by a transverse vertical thin gusset wall 28 and a top mounting flange wall 30. Ankle portion 12 joins the forefoot at a downwardly and rearwardly sloping transition wall 32 that supports the forefoot portion 16 and defines the points of commencement of the plurality of slots 20 and precurved bending members 21a through 22d and a rigid lowermost wall 64 as illustrated. Vertical attachment bore 34 is both shown in FIGS. 2 and 3 and opens at the upper end through the upper face of mounting flange wall 30 of ankle portion 12 and opens at the lower end into a counter bare 36 that extends downwardly through the bottom of the keel for accommodating the head of an attachment bolt or the like which bears against a molded in place washer 40 in a manner conventional and known per se. Ankle portion 12 also has another thin vertical gusset wall 29 centered along the keel's longitudinal axis in line with the axis of vertical attachment bore 34 and counterbore 36 and orthogonal to gusset wall 28 for further structural reinforcement of annular wall 26 and ankle portion 12. In the vertical cross sectional view of FIG. 3, the section line passes through this gusset wall 29 in the ankle portion 12.

To the rear of the vertical attachment axis defined by annular wall structure 26, a diminished heel portion 14 is formed by an upwardly and rearwardly sloping thin heel wall 40 that is preferably serrated or furrowed an the rearward face at 41 for improved adhesion of the foamed cover. Diminished heel wall 40 merges with the rearward extent of the top wall 30 of ankle portion 12. The lower extent of heel wall 40 merges with the rearward extent of the sole plate 24 that is part of forefoot portion 16. As shown in FIGS. 1 and 2, the counter bore 36 passes upwardly into ankle portion 12 at the junction of these walls of the heel portion 14 and forefoot portion 16.

Now with respect to the controlled bending and hence progressive stiffening of the forefoot portion 16, an instep surface 42 that also forms the upward surface of the uppermost bending member 22a has a gentle forward and downward curvature about a center of revolution that preferably is located above and forward of the forefoot portion as best illustrated in FIG. 3. The radius R, is used to designate the radius of the instep surface curvature and in this embodiment is on the order of and preferably somewhat greater than the overall length 1 of keel 10. In order to define the forwardly tapering profile in the vertical plane of the forefoot portion 16, the curved bottom surface 44 of sole plate 24 may have a different center of revolution than the instep and is generally above the forefoot but to the rear of the center of curvature of the instep surface 42. This geometry causes these surfaces to converge in their curvature toward and terminate at a tip 50 that projects as a solid (unslotted) tip 52 of sole plate 24. While the radii of curvatures of instep surface 42 and bottom surface 44 could be equal, in this embodiment the radius of a curvature of bottom surface 44 is about 1.25 times the radius of the instep surface 42 and the center of the curvature of bottom surface 44 is about 0.251 rearward of the center of rotation of instep surface 42.

Arcuate slots 20 have in this embodiment the same center of revolution as instep surface 42 and are formed at equal increments of increasing radii and hence depth below surface 42 in accordance with the nature of injection molding prosthesis to produce a structure of superposed thin walls, in this instance the precurved bending wall members 22a through 22d separated or gapped by the slots 20. These bending members are anchored at their fore and aft ends and are initially separated or spaced by slots 20 so their midbody portions are free to bend under bonding moments and axial compression. In this embodiment with the radius $R_1$ representing the curvature of instep surface 42, corresponding surfaces of precurved bending members 22a through 22d are disposed at increasing integer multiples of dimension d so that for example the upper surface of member 22b is at $R_1+d$ and that of members 22c in at $R_1+2d$, etc.

Slots 20 terminate at their rear extent in end pockets 60 rounded in the vertical plane and being substantially equidistant from the opposite faces of transition wall 32 as best shown in FIG. 1. The transitions of bending members 22a through 22d into wall 32 are upwardly curved in relatively gentle radius $R_3$ bends to minimize stress concentration and likewise the upper instep surface 42 has a corresponding bend radius $R_3$. The forward extents of slots 20 terminate in rounded end pockets 62 truncated along the lowermost portions to maintain a uniform wall thickness for sole plate 24 relative to bottom surface 44 as indicated. Bending member 22d overlies a lowermost wall 64 (see FIG. 1) of forefoot portion lying just above a triangular slot 66 and is not a bending member but forms a substantially rigid structure reinforced by a vertical central gusset wall 68. Wall 64 does not bend significantly during keel deflection but rather forms a structural bottom constraint against which the lowermost bending member 22d can stack under the largest of keel deflections.

The overall width of keel 10 is shown in FIG. 2 to be substantially uniform except that in the preferred embodiment the side walls 70 and 72 of forefoot portion 16 commence an upward and inward taper at approximately the elevation of the bottom of rigid ankle portion 12.

It is observed that the geometry of forefoot portion 16 with the converging instep surface 42 and bottom surface 44 dictate that the are lengths of slots 20 and hence the lengths of bending members 22a through 22d decrease at successively lower slot and member positions. By this configuration, the upper bending members beginning with 22a are the longest and have the least stiffness and hence provide the least resistance to bending and axial compression loads when the foot is deflected by a load (see FIG. 6a) applied near tip extension 52. Those bending member at increasing depth below instep surface 42 are shorter and have greater stiffness and are less yielding to axial compression and bending loads and offer increased resistance to the controlled bending.

Figure 4:
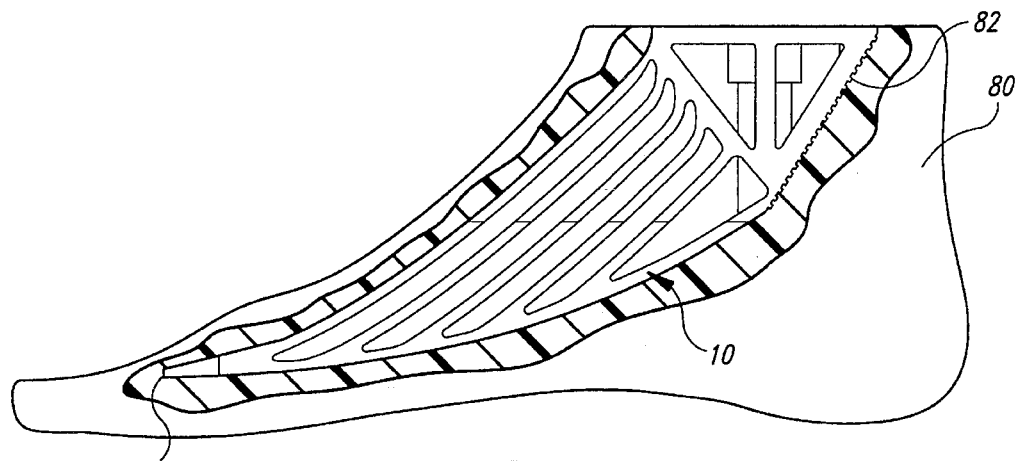
FIG. 4 in an assembled view of the prosthetic foot showing a foamed cosmesis in the shape of a human foot having a breakaway section to illustrate the placement of the internal keel within the cover.
Figure 5:
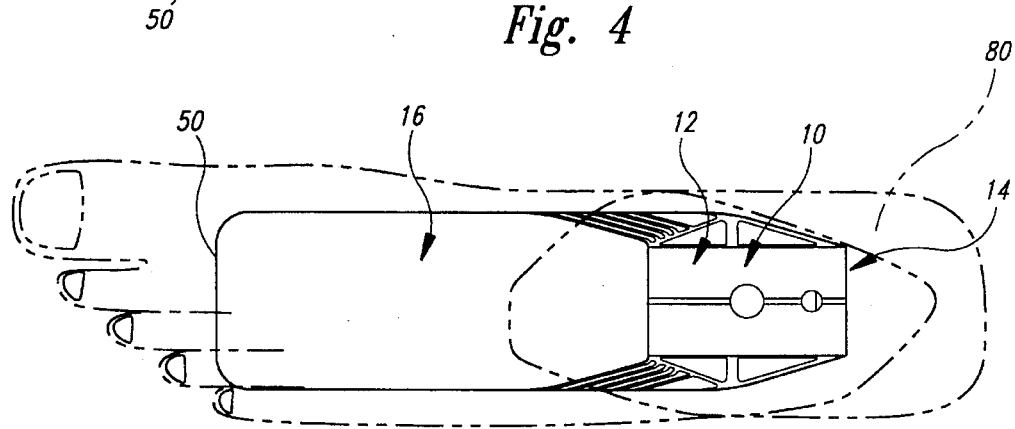
FIG. 5 is a top plan view of the assembled cosmesis and keel in which the dotted lines represent the profile of the foamed cosmesis.

FIGS. 4 and 5 show keel 10 assembled with a foamed polymer cover 80 of a relatively low density foam material, known per se, and bonded to the exterior surface of keel 10. The serrations 82 on the rear surface of keel portion wall 40 provide durable long life adhesion of the foam in the heel area to the keel. The tip 50 of the keel may extend into the region of too separation of the cosmesis cover 80 as indicated. Alternatively smaller keels may be used in larger foot covers with acceptable performance in which case the keel tip may not extend as far as shown in FIGS. 4 and 5 and may have a narrower width ratio to the cover than as shown in FIGS. 4 and 5.

To demonstrate the dynamic functioning of keel 10 under different loads, FIGS. 6a–6f show side by side views of the keel 10 unloaded (FIG. 6a) and loaded (FIG. 6b) for 0° orientation of the ankle axis relative to vertical, corresponding, for example, to a standing posture; and intermediate forward ankle rotation of 22° unloaded (FIG. 6c) and loaded (FIG. 6d) and substantially fill forward rotation at 45° at unloaded (FIG. 6e) and loaded (FIG. 6f) conditions, respectively. The configuration of the bending members 22a through 22d of the keel forefoot portion 16 provides an initial softness of the keel when the load is applied at or near the keel tip an illustrated in FIG. 6f. The free space formed by slots 20 allow each bending member to initially deform freely under bending moments and axial compression both of which occur during loading of keel 10. Thus, the initial deflection of the keel forefoot causes the first bending member 22a to deform until it is bent into an increasingly smaller radius of curvature. Ultimately, the bending of member 22a is constrained when its lower face is folded against the next underlying bending member 22b. Thus with further loading and greater deflection, the bending members successively deform and fold or stack up against the next underlying bending member which is illustrated best by the sequence of FIGS. 6c–6d and 6c–6f. The stacking constrains individual bending members and causes progressive stiffening of the keel.

Figure 6A:
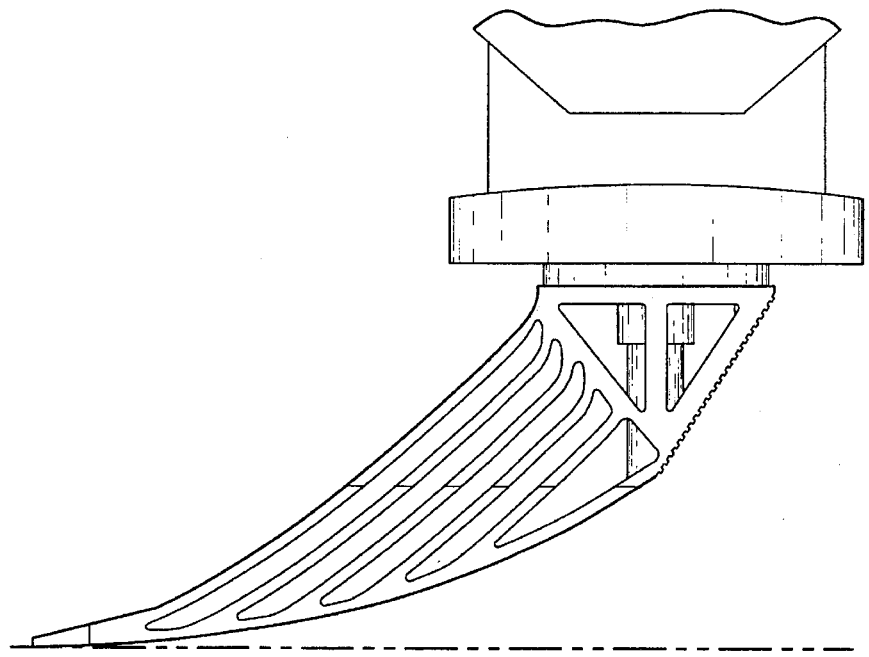
FIGS. 6a, 6b, 6c, 6d, 6e and 6f are a series of side elevation views showing the keel in various unloaded and loaded conditions.
Figure 6B:
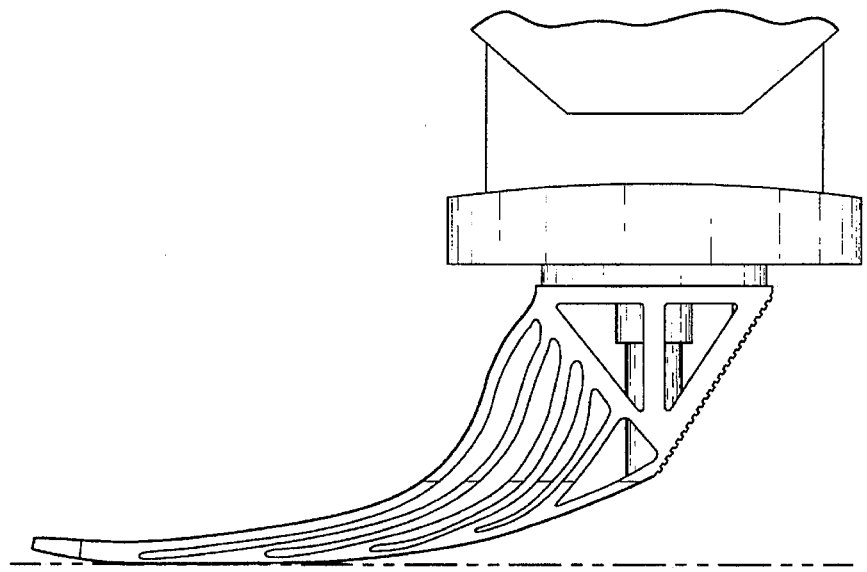
Figure 6C:
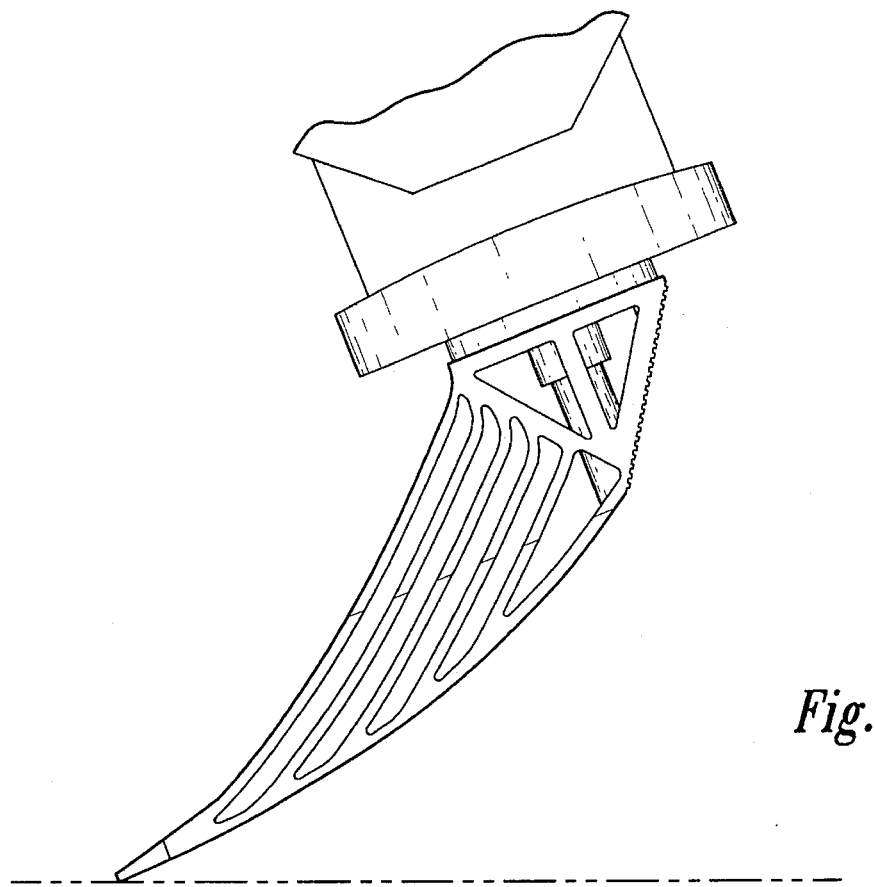
Figure 6D:
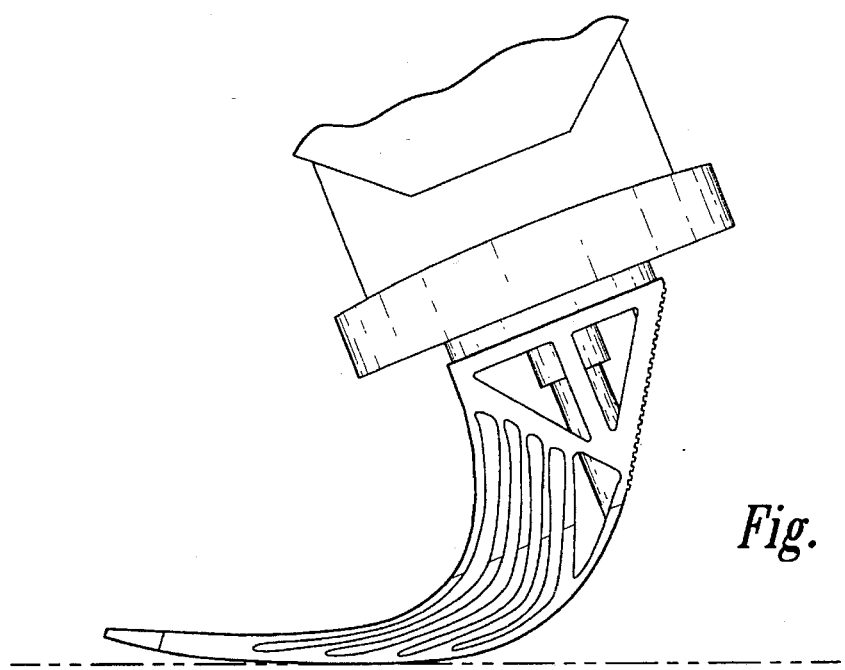
Figure 6E:
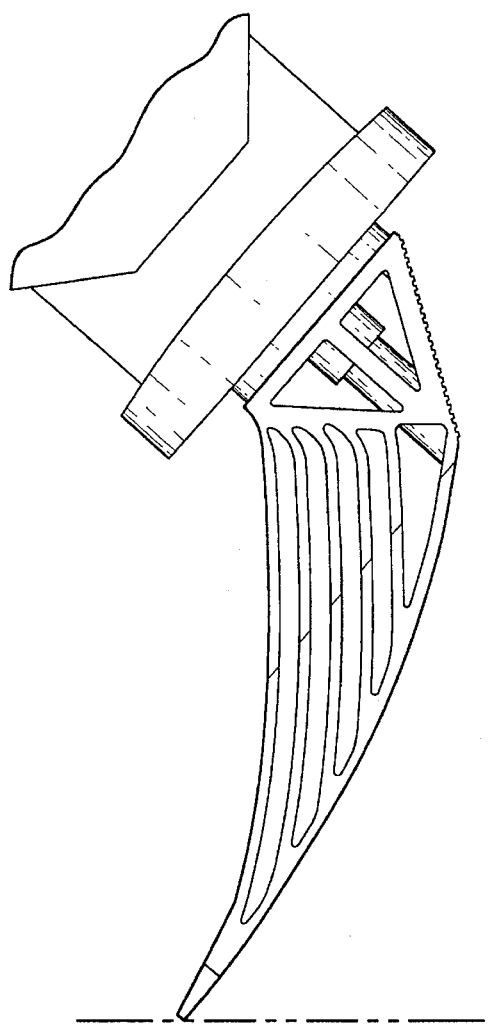
Figure 6F:
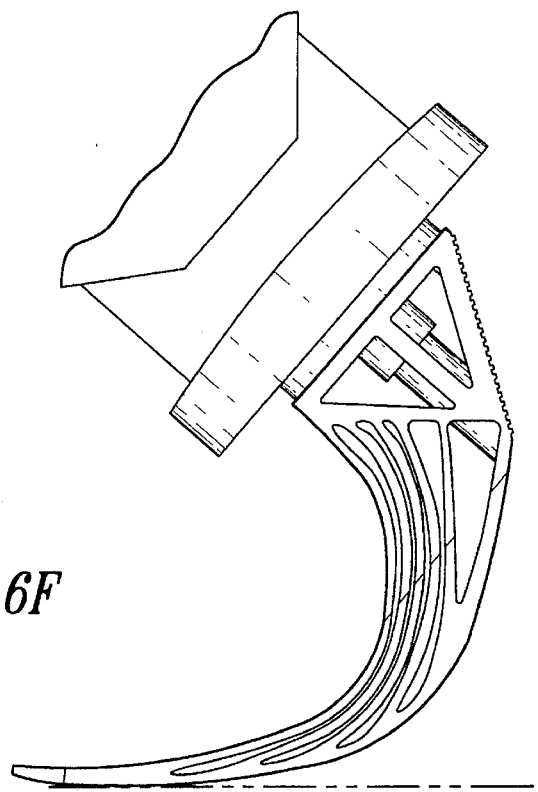

When standing, the load is applied as shown by the sequence of FIGS. 6a to 6b substantially at the center of the forefoot and the keel has a moderate stiffness for comfort. When the load moves forward toward the keel tip, such as occurs during walking, the tip and the individual bending members deflect more readily due to the larger bending moments on these members due to load placement, thereby giving a relatively soft tip feel. When still larger loads cause increased deflection, the above mentioned stacking of the bending members occurs and progressive stiffening of the keel is exhibited. The result is a keel and foot that has moderate stiffness during standing, a soft toe during walking for easy rollover, and that stiffens significantly with larger deflection to support greater foot and body loads when and if needed.

By way of example, the prosthetic foot in accordance with the foregoing disclosure may have a keel made with a polymer such as polyamide (NYLON®) but can be other natural and/or synthetic polymers such as epoxy, urethane, phenolic, unsaturated polyester, polyarylate, polyimide, polyamide-imide pollyacylate, polyester, polyurethane, polycarbonate, polyether, polyetherether ketone, polysulfone, polyplenylene sulfide, polyplenylene oxide, polyolifene, and polyacetal, and well as other materials including metals such as aluminum, titanium, steel and various alloys having different degrees of elastic properties and with or without viscous dampening and with or without fiber reinforcement. Typical ranges of dimension of the keel 10 are" l (length)=4 to 8 inches, w=1 to 4 inches, c=1 to 3 inches, h=1 to 3 inches, $R_1$=5 inches to infinity, $R_2$=5 inches to infinity (i.e. may be straight, R=infinity in certain applications), $R_3$=0.2 to 0.6 inches selected to minimize stress concentrations, d=0.01 to 0.5 inches, and t (wall thickness)=

0.01 to 0.3 inches. Other dimensions may, of course, be used. The material forming the keel may have a modulus of elasticity substantially in the range of $1 \times 10^5$ PSI to $1 \times 10^6$ PSI.

Figure 7:
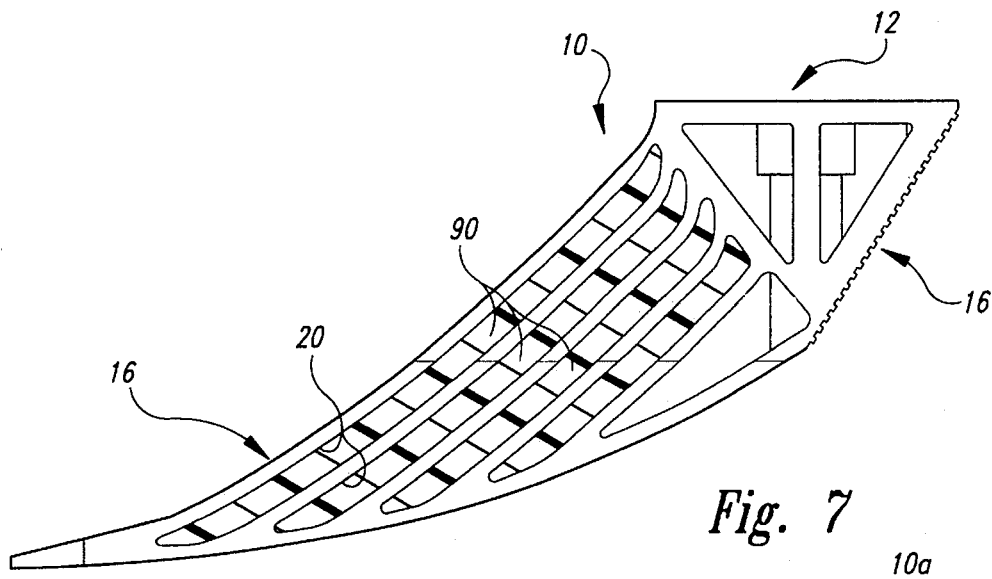
FIG. 7 is a vertical sectional view of an alternative embodiment of the keel having stiffening material disposed in the gaps between bending members.

With reference to FIG. 7, an alternative preferred embodiment is illustrated in which the voids formed by slots 20 are wholly or partially filled with a stiffening material such as a low density elastomeric foam 90. Foam 90 or other stiffening material may be disposed within slots 20 before the keel 10 is covered by the foamed foot cosmesis, or the casting or foaming of the cosmesis itself around the keel can be controlled to inject suitable mounts of foam material into slots 20 to provide the desired level of stiffening.

Furthermore, only portions of the slots 20 or alternate slots 20 may be provided with foam filler thereby selectively meeting the stiffness requirement of a particular patient. Furthermore, different slots 20 may be filled with different elastomers, non-elastomers and/or dampening materials in order to, for example, provide greater stiffness to the uppermost bending members and leaving the lower beading members free to flex under bending and axial compression loads. Further still, an alternative embodiment may provide for a greater or fewer number of bending members 22 depending upon the stiffness and flexure requirements of a particular user. At least one such bending member is required together with an underlying keel structure to limit its bending beyond some preselected curvature to cause the needed stiffening.

Figure 8:
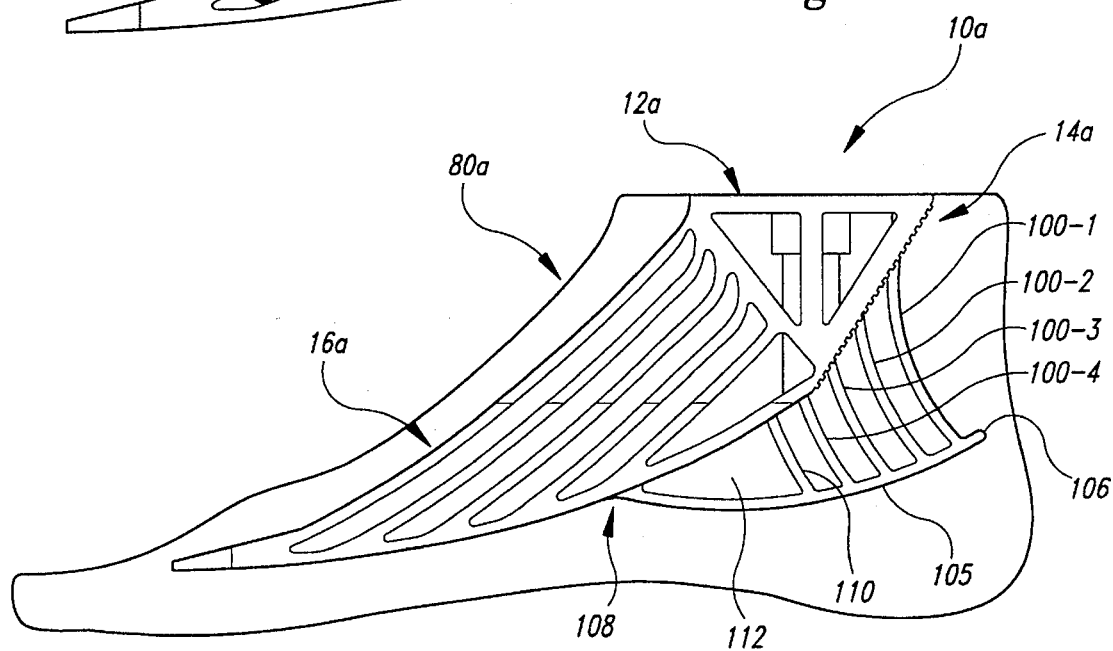
FIG. 8 is a side elevation view of an alternative embodiment of the keel having a heel structure with multiple bending members that function to provide a soft heel spur with progressive stiffening similar to the forefoot structure.
Figure 9:
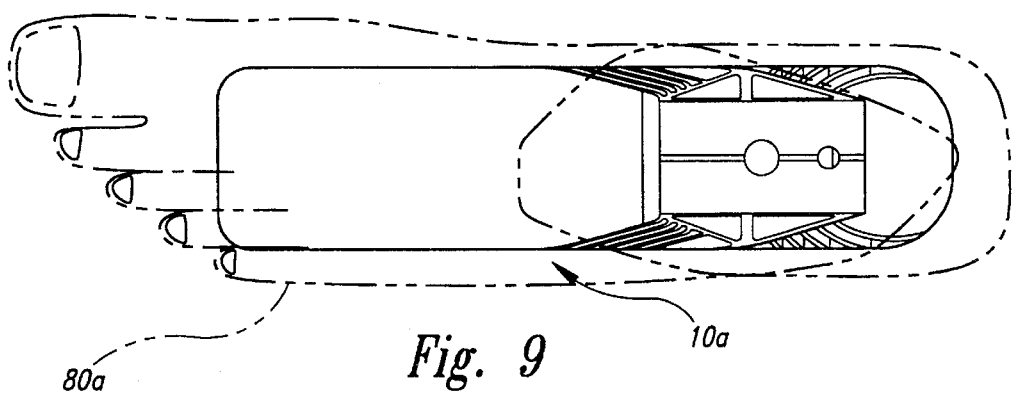
FIG. 9 is a top view of the alternative keel construction of FIG. 8.

FIGS. 8 and 9 show an embodiment of the keel having a heel structure or portion 14' formed with multiple bending members that extend from the rear extent of the ankle portion 12' in relatively large radius arcs (alternatively, these members may be straight, i.e., a radius=infinity) and joined with a heel bottom plate 105 that projects rearwardly from a union with the forefoot sole plate 24' at 108 and terminates at spur end 106. The innermost wall member 110 of this heel structure is substantially non-bending and is reinforced by a center gusset wall 112 in the vertical plane. A heel load applied at or near spur end 106 is reacted in a way similar to a tip load on the forefoot and initiates bending of members 100a, 100b, 100c, etc., which successively stack up and cause the progressive stiffening described above for the forefoot. A standing posture causes the load on the heel structure to be substantially centered in the fore-aft dimension and is reacted by a relatively low bending moments and axial compression loads on the members 100a through 100d.

Figure 10:
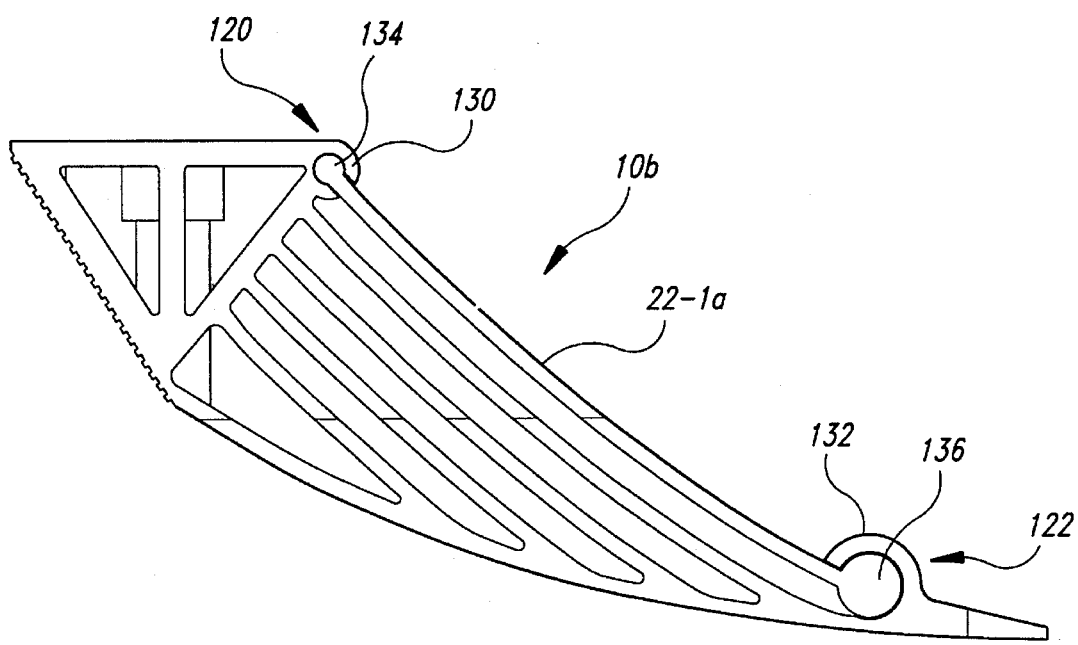
FIG. 10 is another alternative with one of the forefoot bending members being detachable for replacement or substitution.

FIG. 10 is a further alternative embodiment in which the uppermost bending member 22a' of the forefoot is detachable for substituting a member having different stiffness or other properties for further customizing the patient's foot prescription. Here, the ends of member 22a' of the forefoot portion 16" have cylinder and socket connections 120 and 122 which snap lock the member in place on keel 10" prior to applying the comesis. Although a wide variety of connection types may be used, here split cylinder sockets 130 and 132 oriented widthwise of the keel and disposed to receive mating cylindrical protuberances: 134 and 136, respectively, formed on the ends of replaceable member 22a'. Member 22a' may be a different material or thicker, or have other variant properties compared to the fixed bending members 22b', 22c', etc., to change the stress-strain characteristics, or dampening or other characteristics of the keel. Although just one member is shown as detachable hence replaceable in this embodiment, it will be appreciated that a plurality of the members may be replaceable and each may be the same or different for maximum versatility.

As will be apparent to those skilled in the art, the present invention may be embodied in forms other than those specifically disclosed above without departing from the spirit or essential characteristics of the invention. The particular embodiment of the prosthetic foot including keel 10 as described above is therefore to be considered in all respects as being merely illustrative of a prosthetic foot and keel of the present invention. The scope of the invention in set forth in the following claims.

I claim:

1. A keel for a prosthetic foot, comprising:
   a unitary structure formed from a material having elastic properties and having ankle, heel and forefoot portions;
   said ankle portion adapted to receive an attachment means for joining the keel to a user's leg or leg prosthesis;
   said forefoot portion having curved instep and bottom surfaces that commence at respective upper and lower extents of said ankle portion and curve forwardly about centers of revolution located generally above said forefoot portion and that converge toward and terminate at a tip of the keel, said forefoot portion having side walls that extend between said instep and bottom surfaces;
   a curved sole plate defining said curved bottom surface of said forefoot portion;
   a plurality of arcuate slots formed in said forefoot portion and extending widthwise and opening at said side walls, said slots curving generally about said centers of revolution and lying at different depths beneath said instep surface to define a plurality of normally spaced apart thin wall precurved bending members having rearward and forward extents that are connected to and constrained at said rearward extents by said ankle portion and at said forward extents by said sole plate, said bending members being configured so that with increasing body load on and deflection of the keel said bending members react to bending and axial compression loads by successively stacking up against an adjacent bending member thereby progressively increasing the stiffness of the keel.

2. The keel of claim 1, further comprising selective stiffening means disposed in at least one of said arcuate slots for selectively increasing the stiffness of said forefoot portion in reaction to said increasing body load and keel deflection.

3. The keel of claim 2 wherein said stiffening means comprises a compressible elastomeric filler disposed in said at least one of said arcuate slots.

4. The keel of claim 1 wherein said material is a synthetic polymer having a modulus of elasticity substantially in a range of $1 \times 10^5$ PSI to $1 \times 10^6$ PSI and said unitary structure is formed by injection molding of said synthetic polymer so as to form said arcuate slots and thereby define said bending members as relatively thin wall webs.

5. The keel of claim 1 wherein said forefoot portion is of substantially uniform width from said keel portion to said tip and said plurality of arcuate slots extend widthwise across said substantially uniform width so that said plurality of thin wall precurved bending members have a length, width and thickness, said length and said width are both substantially greater than said thickness.

6. The keel of claim 1 wherein said plurality of arcuate slots formed in said forefoot portion are of decreasing arc length along said forefoot portion at successively lower slot positions beneath said instep surface so that uppermost bending members defined by those of said arcuate slots closest to said instep surface have a lesser resistance to said bending and axial compression loads and lower bending members have increased resistance to said bending and axial compression loads due to relative shorter length.

7. The keel of claim 1 wherein said plurality of arcuate slots formed in said forefoot portion have curvatures, said curvatures of said slots being substantially equal to a curvature of said curved instep surface.

8. The keel of claim 1 wherein said centers of revolution comprise a first center of revolution defining a curvature of said curved instep surface and a second center of revolution of greater radius defining said curved bottom surface.

9. The keel of claim 8 wherein said first center of revolution lies above and forward of said forefoot portion of said keel, and said second center of revolution lies above said forefoot portion and rearward of said first center of revolution.

10. The keel of claim 9 wherein said arcuate slots curve downwardly and forwardly terminating at spaced intermediate locations along said sole plate so that loading of said keel forces said keel sole to bend into a shortened radius of curvature which forces successive bending members into shortened radii of curvatures so that said sole and bending members collectively assume minimum stress curvatures.

11. The keel of claim 1 wherein said ankle portion has a substantially vertical attachment bore and forefoot portion extends forwardly of said vertical attachment bore and said heel portion projects to Me rear of said vertical attachment bore, and wherein said heal portion has the shape of a diminished human heel and defines a rearwardly and upwardly sloping end surface extending from its forward extent as a continuation of the curved bottom surface of said forefoot portion commencing substantially at vertical attachment bore and terminating at a rearmost extent of an upper surface of said ankle portion.

12. The keel of claim 1 wherein said unitary structure is molded by an injection molding process from a synthetic polymer so that the entire unitary structure is defined by thin walls of substantially uniform thickness throughout including said thin wall precurved bending members of said forefoot portion.

13. The keel of claim 1 wherein each of said plurality of arcuate slots are formed with opposite ends having uniformly rounded interior radii so as to minimize stress concentrations during deflection of said keel, and said instep surface having a change in curvature forward of said arcuate slots where the curved instep surface approaches a curvature of said bottom surface to define a substantially uniform vertical thickness of the tip.

14. The keel of claim 1 wherein said plurality of arcuate slots formed in said forefoot portion are arranged in a succession of decreasing length with increasing depth beneath said curved instep surface wherein each arcuate slot has a forward terminus that approaches but terminates at equidistances within said structure above said curved bottom surface.

15. The keel of claim 1 wherein said forefoot portion is joined to said ankle portion in a transition region in which said forefoot portion and said ankle portion have respective widths that are upwardly and inwardly tapered.

16. A prosthetic foot comprising a keel according to claim 1 and further comprising a foamed polymer cover having elastic properties and shaped to resemble a human foot, said cover encasing said unitary structure.

17. The prosthetic foot of claim 16 wherein said foamed polymer cover comprises a polymer material of lower density than said material from which said unitary structure is made and said polymer cover is cast onto said keel, so as to at least partially occupy at least one of said arcuate slots thereby increasing stiffness of said forefoot portion by causing said bending of said bending members to compress said polymer material of said lower density within said arcuate slots.

18. The keel of claim 1 wherein at least one of said bending members comprises connector means at least on one of its ends for detachable connection to said structure.

19. The keel of claim 18 wherein said connector means comprises snap lock pocket and protuberance means.

20. The keel of claim 1 wherein at least one of said bending members has means for detachable connection to said structure so that selectively different bending members are exchangeable with said bending member having means for detachable connection.

21. A keel for a prosthetic foot, comprising:

an ankle portion adapted to be attached to a user's leg or leg prosthesis;

a sole plate connected to said ankle portion and extending forwardly therefrom, at least a portion of said sole plate being adapted to flex relative to said ankle portion;

a first support rib extending from said sole plate at a location forward of said ankle portion to said ankle portion at a location above a connection between said ankle portion and said sole plate, said rib having elastic properties to allow said sold plate to flex when a load is applied to said sole plate and to restore said sole plate to a neutral configuration when said load is removed; and a second support rib extending from said sole plate to said ankle portion, said first and second support ribs being positioned parallel to each other so that said ribs are connected to said sole plate at locations that are spaced apart from each other and said ribs are connected to said ankle portion at locations that are spaced apart from each other whereby said ribs successively contact each other to increase a resistance to flexing of said sole plate as a flex of said sole plate increases with increasing load applied to said sole plate.

22. The keel of claim 21 wherein at least one of said support rib has visco-elastic properties to dampen a resilient movement of said support rib.

23. The keel of claim 21 wherein said sole plate is resilient and flexible so that the resilience of said sole plate assists said support rib in restoring said sole plate to said neutral configuration when said load is removed.

24. The keel of claim 21 wherein said ankle portion, sole plate, and support rib are integrally formed defining a monolithic structure.

* * * * *

UNITED STATES PATENT AND TRADEMARK OFFICE
CERTIFICATE OF CORRECTION

PATENT NO. : 5,549,711
DATED : August 27, 1996
INVENTOR(S) : William E. Bryant

It is certified that error appears in the above identified patent and that said Letters Patent is hereby corrected as shown below:

In column 9, claim 11, line 24, please delete "Me" and insert therefor --a--.

In column 9, claim 11, line 25, please delete "heal" and insert therefor --heel--, and delete "the" and insert therefor --a--..

In column 9, claim 11, line 29, following "at" please insert --said--.

Signed and Sealed this

Twenty-first Day of January, 1997

Attest:

BRUCE LEHMAN

*Attesting Officer*        *Commissioner of Patents and Trademarks*